(12) United States Patent
Ronen et al.

(10) Patent No.: US 12,029,912 B2
(45) Date of Patent: *Jul. 9, 2024

(54) OCULAR POSITIONING SYSTEM FOR USE WITH MAGNETIC TREATMENT APPARATUS

(71) Applicant: EPITECH MAG LTD., Yokneam Illit (IL)

(72) Inventors: Itzik Ronen, Nirit (IL); Tomer Carmeli, Alonei Abba (IL); Rafi Giveon, Hod Hasharon (IL); Eitan Sharif, Kibbutz Gesher Haziv (IL)

(73) Assignee: EPITECH MAG LTD., Yokneam Illit (IL)

( * ) Notice: Subject to any disclaimer, the term of this patent is extended or adjusted under 35 U.S.C. 154(b) by 289 days.

This patent is subject to a terminal disclaimer.

(21) Appl. No.: 17/497,299

(22) Filed: Oct. 8, 2021

(65) Prior Publication Data

US 2022/0096858 A1 Mar. 31, 2022

Related U.S. Application Data

(63) Continuation of application No. 16/773,323, filed on Jan. 27, 2020, now Pat. No. 11,141,601.

(51) Int. Cl.
*A61N 2/02* (2006.01)
*A61N 2/00* (2006.01)

(52) U.S. Cl.
CPC ............... *A61N 2/02* (2013.01); *A61N 2/004* (2013.01)

(58) Field of Classification Search
CPC .......... A61N 2/004; A61N 2/02; A61N 2/002; A61N 2/006; A61N 2/06; A61N 2/00; A61N 1/36046; A61N 1/0543
See application file for complete search history.

(56) References Cited

U.S. PATENT DOCUMENTS 5,830,139 A 11/1998 Abreu
6,926,660 B2 8/2005 Miller
(Continued)

FOREIGN PATENT DOCUMENTS

EP     1 006 892 B1   6/2009
WO     2014/181327 A1  11/2014
WO     2021/152574 A1   8/2021

OTHER PUBLICATIONS

Office Action together with an English summary dated Dec. 8, 2020, which issued during the prosecution of Japanese Patent Application No. 2018-538723.
(Continued)

*Primary Examiner* — Christine H Matthews
(74) *Attorney, Agent, or Firm* — Hybrid Law Group P.C.

(57) ABSTRACT

An ocular positioning system for use with a magnetic treatment apparatus for treating an eye of a subject is provided, where the magnetic treatment apparatus includes a magnetic coil for generating a magnetic field and an electric field. The ocular positioning system includes a housing having a proximal end and a distal end, wherein the magnetic coil is disposed in the housing near the proximal end. A positioning member is at least partially attached to the housing proximal end, the positioning member including a base and an eyecup coupled thereon, where the eyecup is configured to receive an orbital region of the subject. At least one sensor is connected to the housing and in electrical communication with the magnetic coil, wherein when the at least one sensor detects the positioning member then the magnetic coil is capable of being activated for treatment.

19 Claims, 8 Drawing Sheets

(56) References Cited

U.S. PATENT DOCUMENTS

| | | |
|---|---|---|
| 9,681,841 B2 | 6/2017 | Riehl et al. |
| 11,141,601 B2 | 10/2021 | Ronen et al. |
| 2009/0182312 A1 | 7/2009 | Gertner et al. |
| 2010/0239067 A1 | 9/2010 | Gertner et al. |
| 2010/0249488 A1 | 9/2010 | Kardos et al. |
| 2014/0257433 A1 | 9/2014 | Ackermann et al. |
| 2015/0085249 A1 | 3/2015 | Abreu |
| 2016/0067086 A1 | 3/2016 | Tedford et al. |
| 2017/0131765 A1 | 5/2017 | Perek et al. |
| 2019/0344076 A1 | 11/2019 | Irazoqui et al. |
| 2021/0228897 A1 | 7/2021 | Ronen et al. |

OTHER PUBLICATIONS

International Search Report and a Written Opinion both dated Jul. 14, 2021, which issued during the prosecution of Applicant's PCT/IL2021/050035.

Notice of Allowance dated Sep. 15, 2021, which issued during the prosecution of U.S. Appl. No. 16/773,323.

Notice of Allowance dated May 28, 2021, which issued during the prosecution of U.S. Appl. No. 16/773,323.

OCULAR POSITIONING SYSTEM FOR USE WITH MAGNETIC TREATMENT APPARATUS

REFERENCE TO RELATED APPLICATIONS

The present application is a continuation application of U.S. patent application Ser. No. 16/773,323, filed Jan. 27, 2020, entitled "OCULAR POSITIONING SYSTEM FOR USE WITH MAGNETIC TREATMENT APPARATUS", now U.S. Pat. No. 11,141,601, the disclosure of which is hereby incorporated by reference.

TECHNICAL FIELD

Embodiments relate to an ocular positioning system for use with a magnetic treatment apparatus for treating an eye of a subject.

BACKGROUND

The effects of magnetic fields have been employed in various medical treatments. An important treatment target is epithelial tissue, as epithelial tissue surfaces constitute a mechanical barrier against external harmful factors. For example, in the eye, corneal epithelium blocks the penetration of harmful substances, as well as polarized substances such as water and ions, into the anterior chamber, and an impairment in the corneal barrier leads to pain, chronic symptoms, injury, or even vision loss.

Use of magnetic fields can be effective for the treatment of eye disorders such as dry eye disease (keratitis sicca), corneal keratitis, corneal epithelial dysfunctions, reduced barrier function of the cornea associated with diabetes, conditions associated with increased corneal permeability due to aging, minor lesions of the corneal surface, conditions associated with wearing contact lenses, reduced self-healing capabilities of the cornea, penetration of harmful agents to the eye from the contaminated environment, weakened anti-penetration system, and cornea-associated inflammation.

Existing systems for treating eye disorders with magnetic fields have drawbacks, such as failing to assure that the subject is positioned properly for administering treatment. In addition, the variability in the anatomical structure of the orbital region between subjects may lead to improper positioning of the eye to be treated in relation to the magnetic field generator. These variations can cause inconsistencies in the treatment since the effectiveness of the treatment is dependent on the positioning of the electromagnetic field.

SUMMARY

In one or more embodiments, an ocular positioning system for use with a magnetic treatment apparatus for treating an eye of a subject is provided, where the magnetic treatment apparatus includes a magnetic coil for generating a magnetic field and an electric field. The ocular positioning system includes a housing having a proximal end and a distal end, wherein the magnetic coil is disposed in the housing near the proximal end. A positioning member is at least partially attached to the housing proximal end, the positioning member including a base and an eyecup coupled thereon, where the eyecup is configured to receive an orbital region of the subject. At least one sensor is connected to the housing and in electrical communication with the magnetic coil, wherein when the at least one sensor detects the positioning member then the magnetic coil is capable of being activated for treatment.

In one or more embodiments, an ocular positioning system for use with a magnetic treatment apparatus for treating an eye of a subject is provided, where the magnetic treatment apparatus including a magnetic coil for generating a magnetic field and an electric field. The ocular positioning system includes a housing having a proximal end and a distal end, wherein the magnetic coil is disposed in the housing near the proximal end. A positioning member is at least partially attached to the housing proximal end, the positioning member including a base and an eyecup coupled thereon. The eyecup is configured to receive an orbital region of the subject, wherein a center of the eyecup is offset from a center of the base.

In one or more embodiments, a magnetic treatment apparatus for treating an eye of a subject includes a housing having a proximal end and a distal end, and a magnetic coil disposed in the housing near the proximal end. A positioning member is at least partially attached to the housing proximal end, the positioning member including a base and an eyecup coupled thereon. The eyecup is configured to receive an orbital region of the subject, wherein a center of the eyecup is offset from a center of the base. At least one sensor is connected to the housing and in electrical communication with the magnetic coil, wherein when the at least one sensor detects the positioning member then the magnetic coil is capable of being activated for treatment.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Embodiments disclosed herein relate to an ocular positioning system for positioning the eye of a subject for treatment with a noninvasive, non-contact magnetic treatment apparatus. Using such an apparatus, an afflicted tissue, such as ocular tissue, may be treated with magnetic pulses created by a magnetic field generator, such as a magnetic coil. When energized, a magnetic coil creates a magnetic field and this time-changing magnetic field and electric field energy is transferred to the treated tissue. In one non-limiting example, a magnetic treatment apparatus can be used for treating ocular epithelial tissue, such as corneal epithelium in the case of dry eye syndrome. In additional examples, a magnetic treatment apparatus may treat other eye diseases, neurological disorders, conditions associated with pathological proliferation, and pathologies associated with epithelial tissues.

Figure 1:
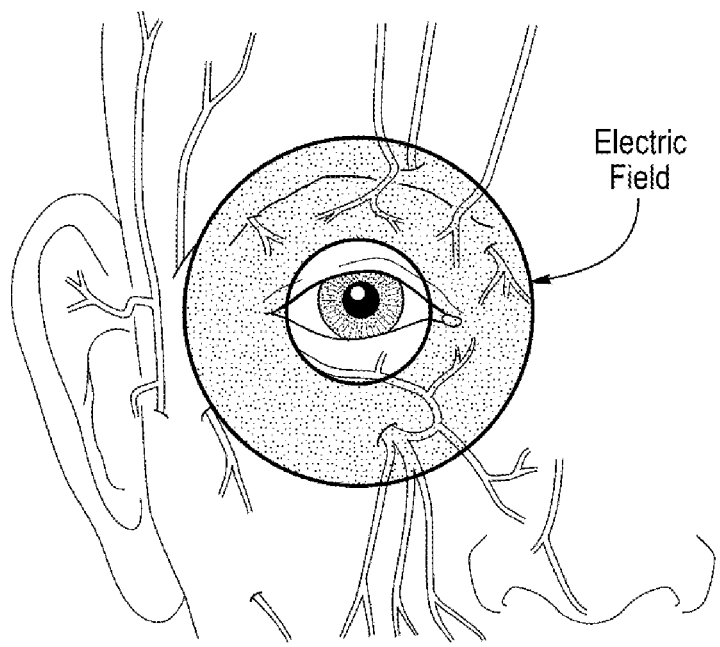
FIG. 1 is a schematic illustration of a general position of an electrical field with respect to a subject's eye and with respect to various nerves innervating the orbital region in the case of a circular magnetic coil in a magnetic treatment apparatus.

In the course of treating ocular tissue, a magnetic treatment apparatus may be used for the electromagnetic stimulation of peripheral nerve tissue in the vicinity of the eye. FIG. 1 is a schematic illustration of an electric field generated by a magnetic coil with respect to a subject's eye and with respect to various nerves innervating the orbital region. During treatment, it is beneficial to stimulate afferent and efferent nerves passing through the foramina around the eye (supraorbital, infraorbital, lacrimal, efferent branches of the facial nerve, innervation of the Orbicularis and Riolan's muscle, etc.). Advantageously, a magnetically-induced electric field can stimulate these nerves simultaneously without the need for any contact.

Figure 2:
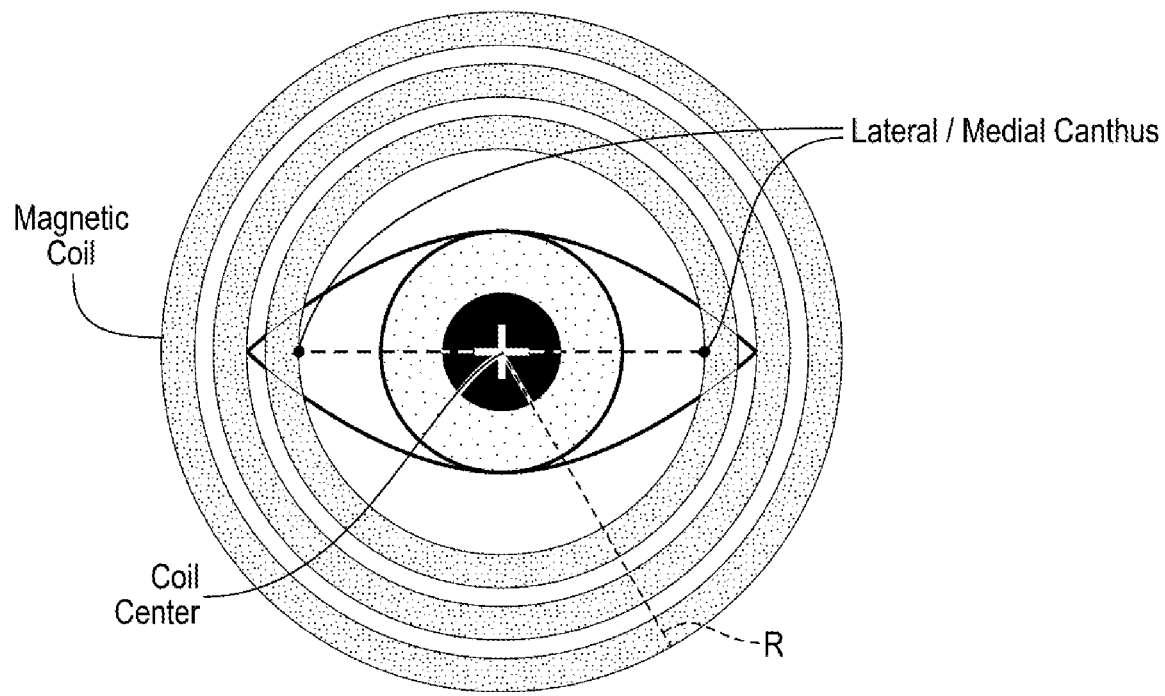
FIG. 2 is a schematic illustration of a desired position of a subject's eye with respect to the example of a circular magnetic coil in a magnetic treatment apparatus.
Figure 3:
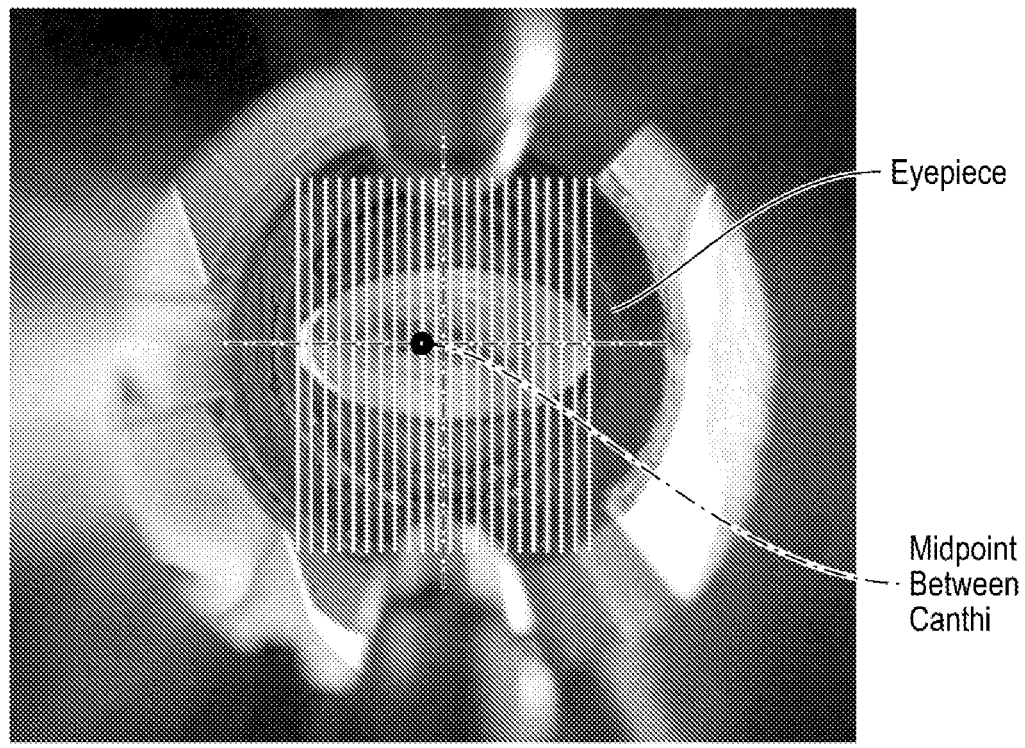
FIG. 3 is a photograph illustrating an offset of the center of a subject's eye with respect to the center of the magnetic coil when an eyepiece is aligned coaxially with the magnetic coil.

The disclosed ocular positioning system ensures accurate, optimal and repeatable positioning and alignment of the subject's eye with respect to a magnetic field generator for effective treatment of ocular tissue. FIG. 2 is a schematic illustration of a desired position of a subject's eye with respect to a magnetic coil in a magnetic treatment apparatus. An eyepiece may be used to engage a subject's orbital region such that the subject's eye can be positioned with respect to the magnetic coil. In one non-limiting embodiment, it may be desirable to have a center of the magnetic coil coaxially aligned with a midpoint between the lateral canthus and medial canthus of the subject's eye, the corners of the eye where the upper and lower eyelids meet, which should also be the center of the subject's eye. However, when the eyepiece is aligned coaxially with the magnetic coil, the midpoint between the lateral and medial canthi is offset from the center of the magnetic coil as illustrated in FIG. 3. As shown, the centers of the eyepiece and the magnetic coil are located at the intersection of the superimposed vertical and horizontal axes, and the midpoint between the lateral and medial canthi of the eye is indicated by the dot offset from the coil center. In one or more embodiments, this offset may generally occur along the horizontal axis.

Figure 4:
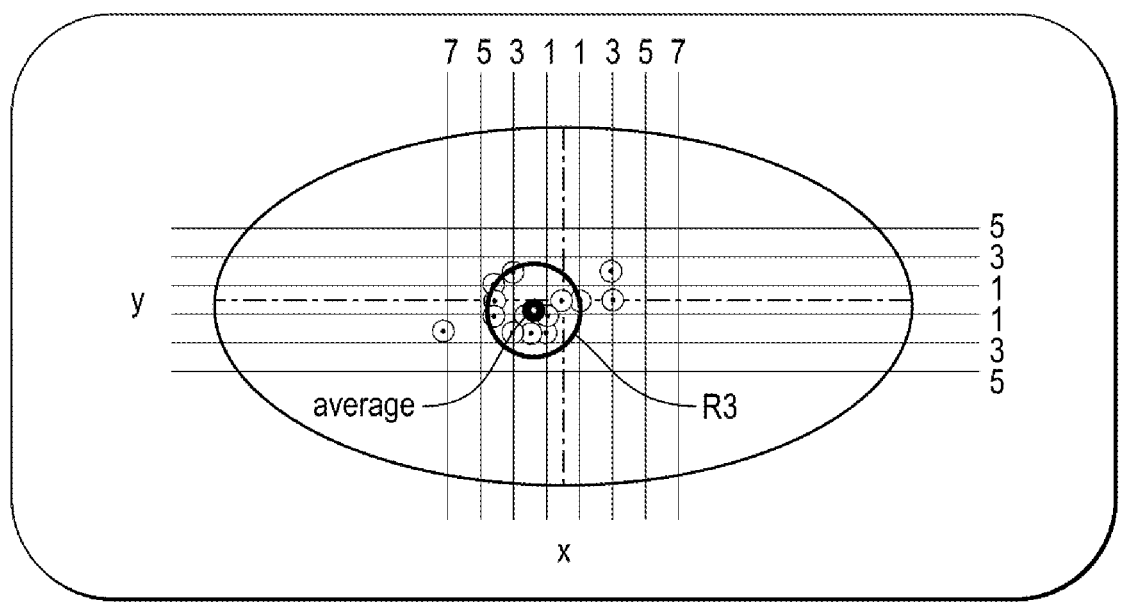
FIG. 4 is a chart showing experimental data of the offset of the center of a subject's eye with respect to the center of the magnetic coil when the eyepiece is aligned coaxially with the magnetic coil.

FIG. 4 is a chart showing experimental data of the offset of the center of a subject's eye (midpoint between the lateral and medial canthi) with respect to the center of the magnetic coil. As in FIG. 3, the vertical (y) and horizontal (x) axes are shown, where the centers of the eyepiece and the magnetic coil are located at the intersection of the axes. The chart also shows a solid elliptical line to represent the perimeter of the eyepiece, and grid lines to represent distances in millimeters away from the common center point of the eyepiece and the magnetic coil. This chart depicts the offset of the midpoint between the canthi and the eyepiece/coil center for 15 subjects, wherein the average offset is calculated to be approximately 3 mm. Such an offset decreases the accuracy and effectiveness of the magnetic treatment.

Figure 5:
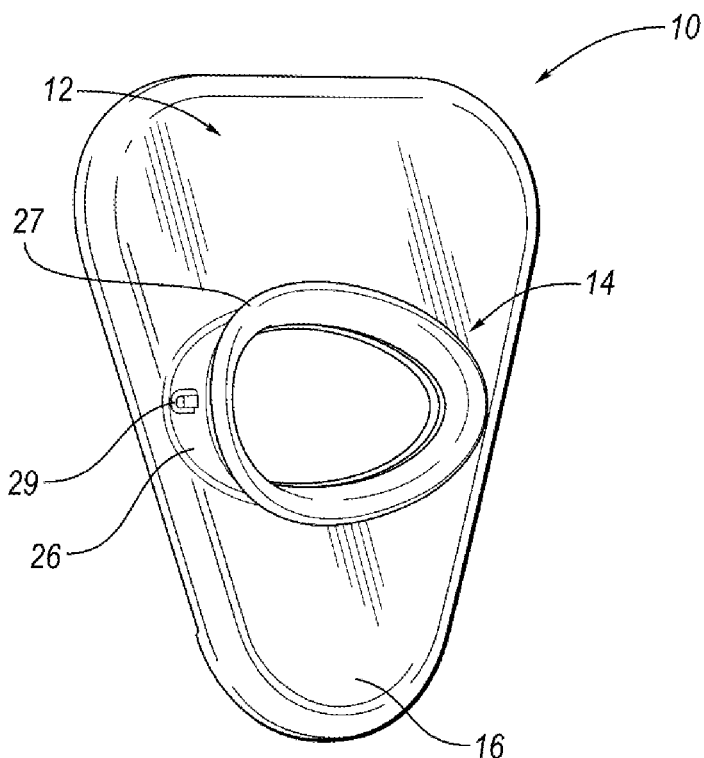
FIG. 5 is a perspective view of a positioning member of an ocular positioning system for use with a magnetic treatment apparatus according to one or more embodiments.

Accordingly, in one non-limiting embodiment, the ocular positioning system disclosed herein may be designed to optimize the position of a subject's eye with respect to the center of the magnetic coil for treatment with a magnetic treatment apparatus. FIG. 5 is a front view of a positioning member 10 of an ocular positioning system for use with a magnetic treatment apparatus according to one or more embodiments. The positioning member 10 includes a generally planar base 12, and in one example may be constructed from silicon. Although the base 12 is depicted herein to be generally triangular in shape, it is understood that this is merely exemplary and that other shapes and configurations are fully contemplated. An eyepiece, such as an eyecup 14, is coupled to an outer side 16 of the base 12 and configured to engage the orbital region of a subject. The eyecup 14 may be integrally formed with the base 12, may be affixed to the base 12 in some manner, or may be removably mounted to the base 12. The eyecup 14 may have the general form of a goggle, and may be generally elliptical in shape as shown, although not limited to this configuration. The eyecup 14 may have a range of sizes as described further below, wherein in a non-limiting embodiment the width may range from approximately 25 mm to 50 mm, and the length may range from approximately 45 mm to 65 mm.

Figure 6:
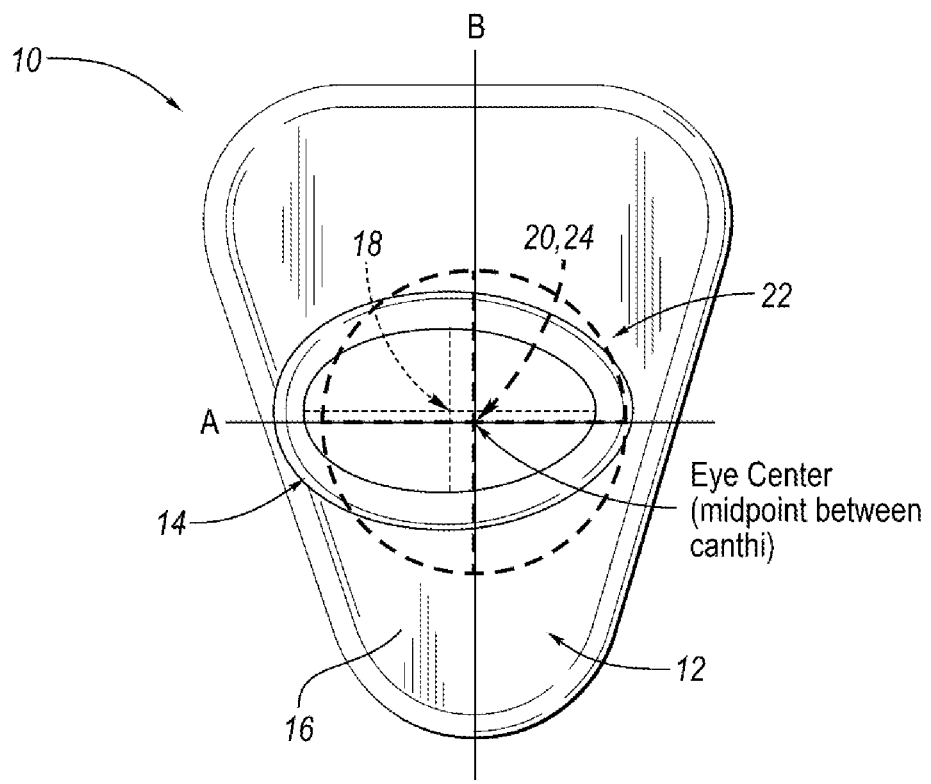
FIG. 6 is a front view of the positioning member of FIG. 5 with the coil center and the eyecup center superimposed thereon.

With reference to FIG. 6, the eyecup 14 is located on the base 12 such that the center 18 of the eyecup 14 is offset from the center 20 of the base 12, either in a horizontal direction, a vertical direction, or both. In the non-limiting embodiment depicted herein, the eyecup center 18 is offset from the base center 20 (and the coil center 24) in a generally horizontal direction, for example, along a horizontal axis A. The center 20 of the base 12 may be determined as a midpoint of the base 12 along the horizontal axis A, a midpoint of the base 12 along a vertical axis B, or an intersection of the horizontal and vertical axes A, B.

FIG. 6 illustrates the positioning member 10 with the perimeter of the magnetic coil 22, the coil center 24, and the eyecup center 18 superimposed thereon. As shown, when the center 24 of the magnetic coil 22 is aligned with the center 20 of the base 12, the center 18 of the eyecup 14 is offset from the center 24 of the magnetic coil 22. The distance between the eyecup center 18 and the base center 20 or between the eyecup center 18 and the coil center 24 may be approximately 3 mm, but is not limited to this distance. This offset of the eyecup center 18 and the base center 20/coil center 24 may allow for the midpoint between the subject's canthi (eye center) to be coaxially aligned with the center 24 of the magnetic coil 22, which may be a more optimal position for treatment.

Figure 7:
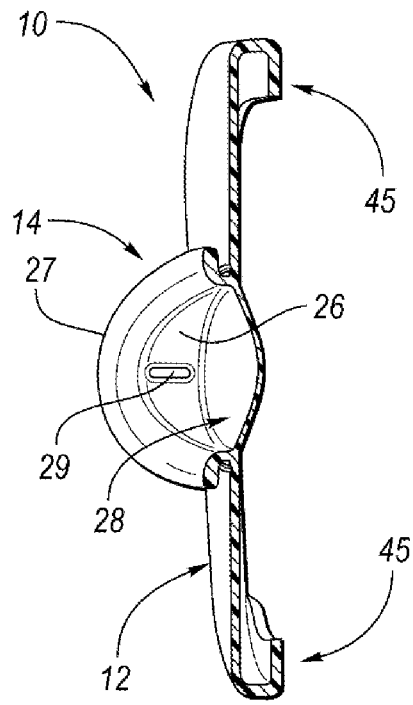
FIG. 7 is a longitudinal sectional view of the positioning member of FIG. 5.
Figure 8:
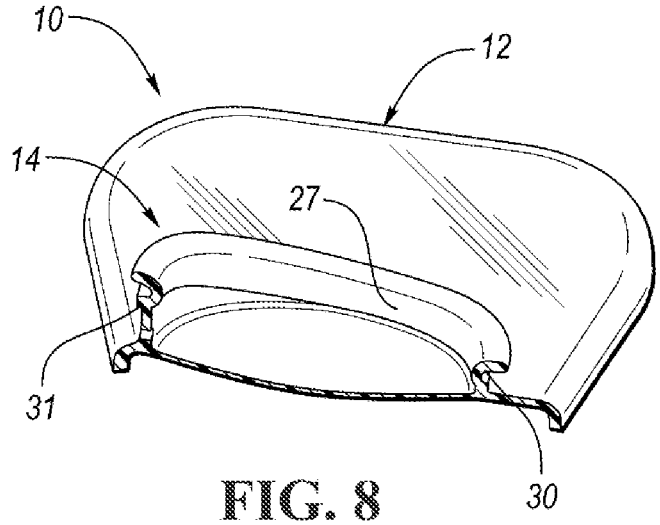
FIG. 8 is a cross-sectional view of the positioning member of FIG. 5.

As shown in FIG. 5 and the sectional view of FIGS. 7 and 8, the eyecup 14 may include a wall 26 extending upwardly from the base 12 and an orbital interface 27 that is formed on and surrounding the upper perimeter of the wall 26. In one embodiment, the eyecup 14 may be constructed from a compressible or deformable material such as, but not limited to, a silicon material capable of conforming to the anatomical structure of the orbital region of the treated subject. The orbital interface 27 thus provides comfort for the subject during treatment, while the wall 26 provides support when pressure is applied to the eyecup 14 by the subject during treatment. In one non-limiting example, the orbital interface 27 may have a thickness of approximately 2 mm.

According to one or more embodiments, the positioning member 10 may be optimally designed for the anatomical structure of the subject in various ways. For example, the eyecup 14 may be constructed according to actual measurements of a subject's eye and surrounding orbital region, thus creating a personalized eyecup 14 for each subject. In another option, a series of eyecups 14 of various sizes may be prepared and each subject fitted for the specific size which best conforms to the subject's anatomical structure. In a further embodiment, an eyecup 14 may be specifically created or fitted for each eye of the subject, e.g. one left eyecup and one right eyecup. The personalized measurements may include, but are not limited to, the length and width of the eyecup and the offset of the center 18 of the eyecup 14 with respect to the center 20 of the base 12.

With reference to FIG. 7, the base 12 may include depressed portion 28 within the eyecup 14 which may accommodate the eyeball of the subject during treatment. The wall 26 may include at least one vent 29 to allow air to flow in and out of the eyecup 14 when the orbital region of the subject is engaged, thus preventing a vacuum from forming. FIG. 8 shows a cross-section of the positioning member 10 which illustrates a variable height of the wall 26 around the eyecup 14 according to one or more embodiments. More particularly, the wall 26 may have a medial wall portion 30 and a lateral wall portion 31 which differ in height. The positioning member 10 shown may be specific to a left eye of a subject, for example, and may have a medial wall portion 30 of lesser height than a lateral wall portion 31. For the left eye positioning member 10 shown, the medial wall portion 30 is on a right side of the base 12 and the lateral wall portion 31 is on a left side of the base 12. This configuration provides an ergonomic interface optimized for the left orbital region of the subject, where the shorter medial wall portion 30 is adjacent the subject's nose. For right eye use, a positioning member 10 may also be provided with a medial wall portion 30 of lesser height than a lateral wall portion 31, although the medial wall portion 30 would be on the left side of the base 12 and the lateral wall portion 31 would be on the right side of the base 12 in this instance.

Figure 9:
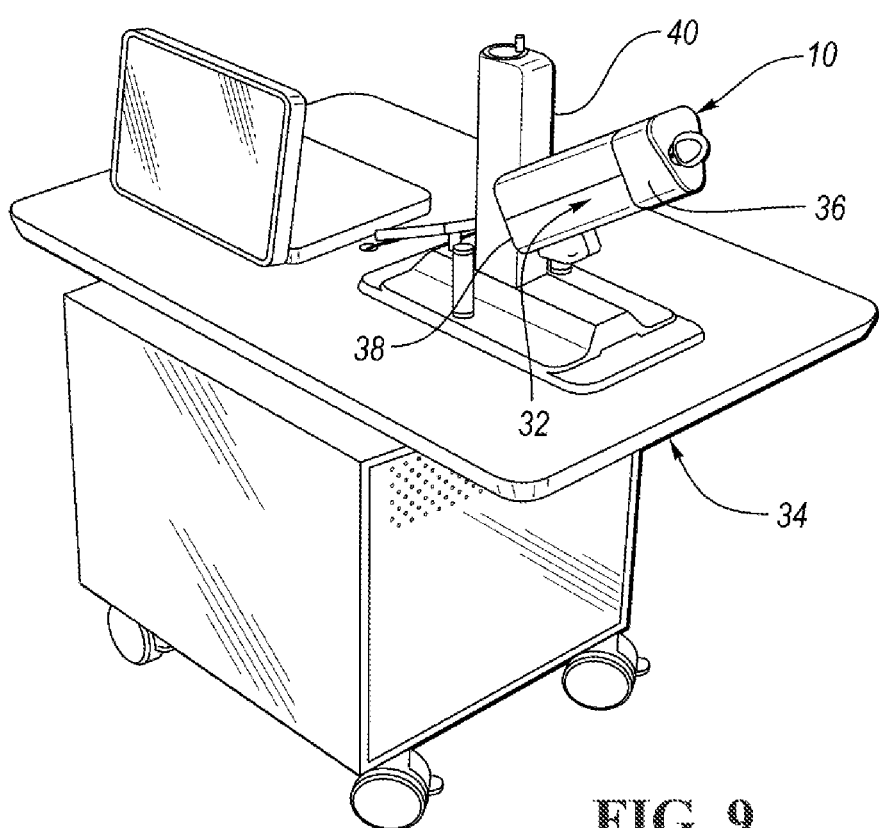
FIG. 9 is an illustration of the positioning member mounted on a magnetic treatment apparatus according to one or more embodiments.
Figure 10:
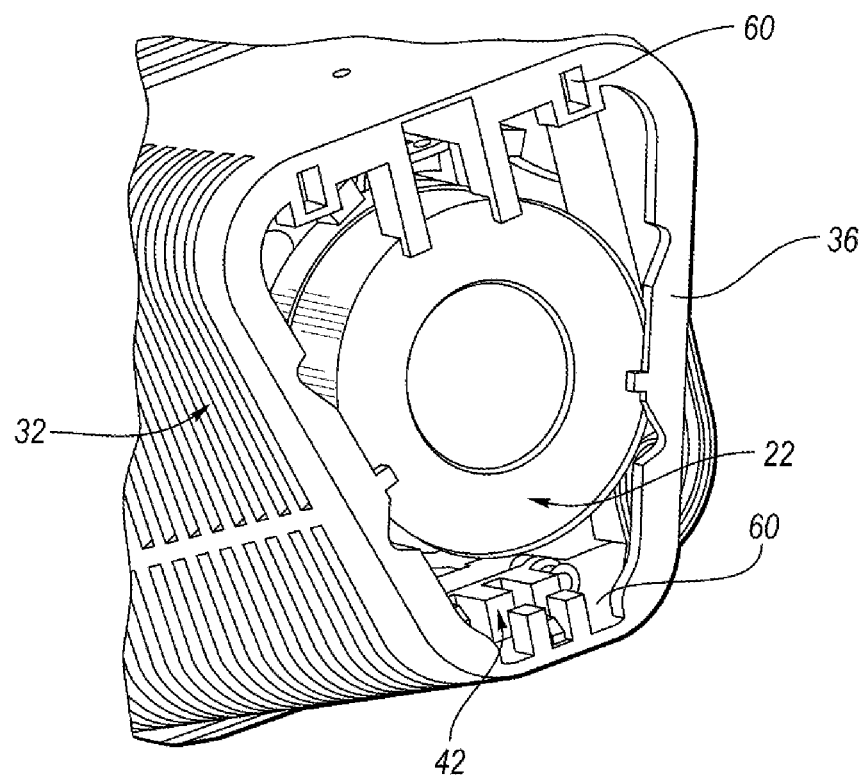
FIG. 10 is a perspective view of a housing with the magnetic coil disposed therein.

FIG. 9 is an illustration of the positioning member 10 mounted on a housing 32 of an exemplary magnetic treatment apparatus 34. The housing 32 has a proximal end 36 to which the positioning member 10 is mounted, and a distal end 38 which may be coupled to an adjustment mechanism 40. The housing 32 may be configured in a fixed or adjustable position to allow the subject's orbital region to engage the positioning member 10 and achieve an accurate, optimal and repeatable eye position relative to the magnetic coil 22 (FIG. 10). The magnetic treatment apparatus 34 shown is configured as a table-top apparatus, although the magnetic treatment apparatus 34 may alternatively be embodied in a hand-held form. Furthermore, although only one positioning member 10 is depicted herein, it is understood that the ocular positioning system (best shown in FIGS. 12-15) and the magnetic treatment apparatus 34 could be constructed to treat both eyes of a subject simultaneously.

FIG. 10 is a perspective view of the housing 32 with the positioning member 10 removed, illustrating the magnetic coil 22. In the magnetic treatment apparatus 34, the magnetic coil 22 is mounted within the housing 32 near the proximal end 36. The magnetic coil 22 produces a magnetic field and directs the magnetic pulses to the treated ocular tissue. In one or more embodiments, a circular or annular magnetic coil 22 may be utilized, although other shapes are fully contemplated. The magnetic coil 22 may have an average winding diameter of about 40 mm, although this dimension is not intended to be limiting. Such a design prevents exposure of ocular tissues such as cornea or retina to high intensity electrical field. The positioning member 10 guides the patient to correctly position the eye or orbital region relative to the magnetic coil 22.

In addition to proper positioning of the subject's eye with respect to the magnetic coil 22, it is also desired to ensure that the magnetic coil 22 is only activated when the subject's eye is in the proper position for treatment. As such, the ocular positioning system disclosed herein not only ensures proper alignment of the subject's eye with the coil center 24, but also employs at least one sensor to ensure that the magnetic coil 22 is only activated if the positioning member 10 is in an optimal position with respect to the magnetic coil 22 and/or the housing 32. Various sensor types, e.g. mechanical, electronic, optical or combinations thereof, are contemplated as described further below, wherein the description of components for each sensor may be equally applicable to the other types of sensors described. In FIGS. 12-15, the ocular positioning system is designated generally by reference numeral 50, and includes the positioning member 10, the housing 32, and the at least one sensor as described below. In one non-limiting embodiment, the housing 32 may be shared by the ocular positioning system 50 and the magnetic treatment apparatus 34, or alternatively the system 50 and apparatus 34 could be housed separately.

With reference to FIGS. 10-13, the at least one sensor may include an optical sensor 42 connected to or disposed within the housing 32. A cover 44 is provided at the proximal end 36 of the housing 32, wherein the cover 44 may be constructed from a plastic material. The base 12 of the positioning member 10 may include a lip 45 (FIG. 7) arranged to receive the cover 44 and facilitate attachment of the base 12 to the cover 44. In this way, the base 12 can be easily received on and removed from the cover 44. In an alternative embodiment, the base 12 and the cover 44 could be permanently attached or integrated into a single piece. In either embodiment, it is understood that the positioning member 10 may be considered to include the cover 44.

Figure 11:
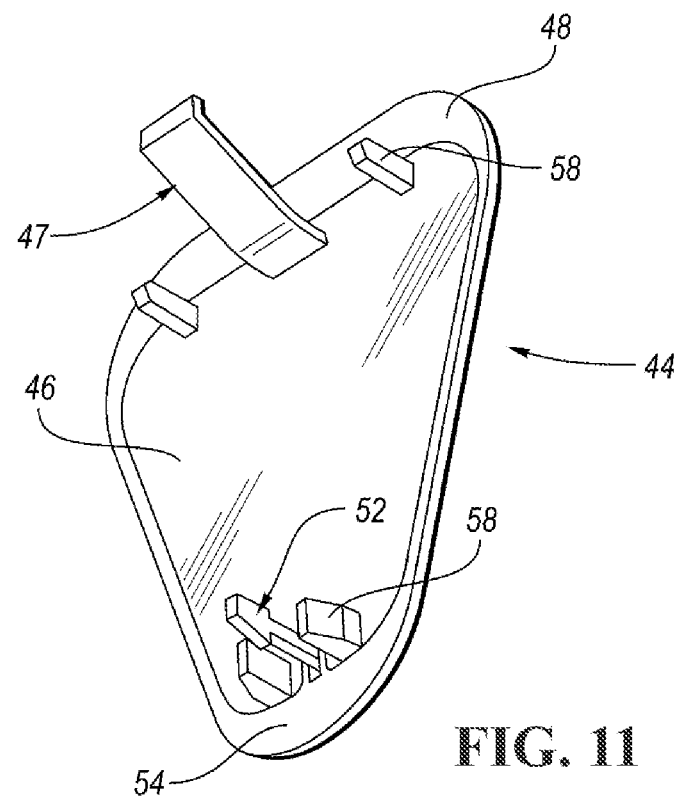
FIG. 11 is a perspective view of a cover for the housing.
Figure 12:
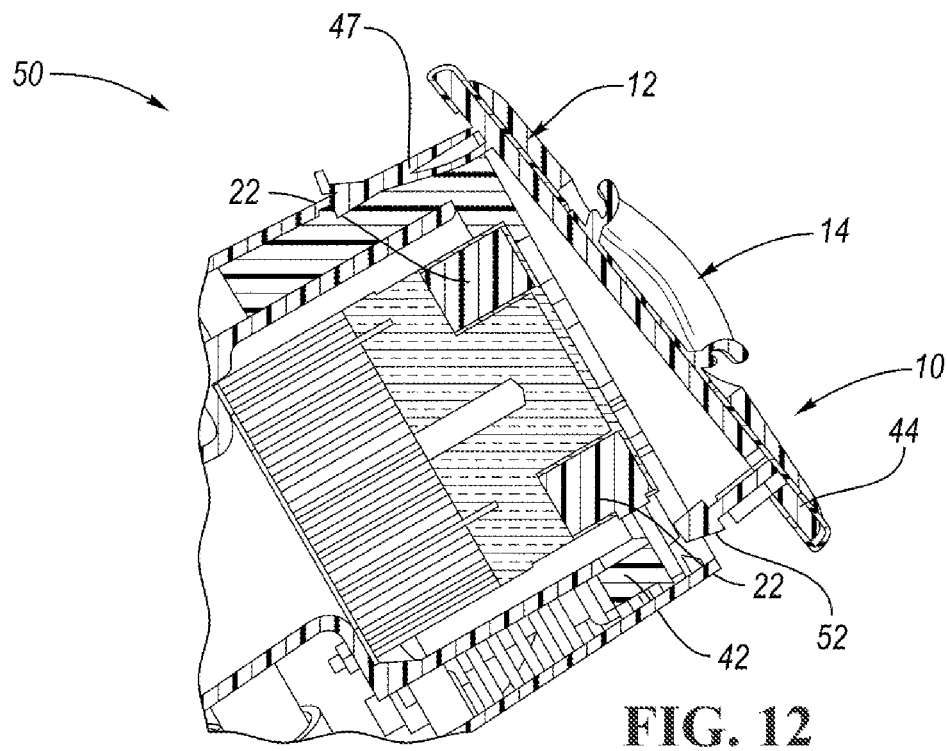
FIG. 12 is a cross-sectional view of the ocular positioning system with the positioning member biased outward away from the housing prior to treatment with the magnetic treatment apparatus.
Figure 13:
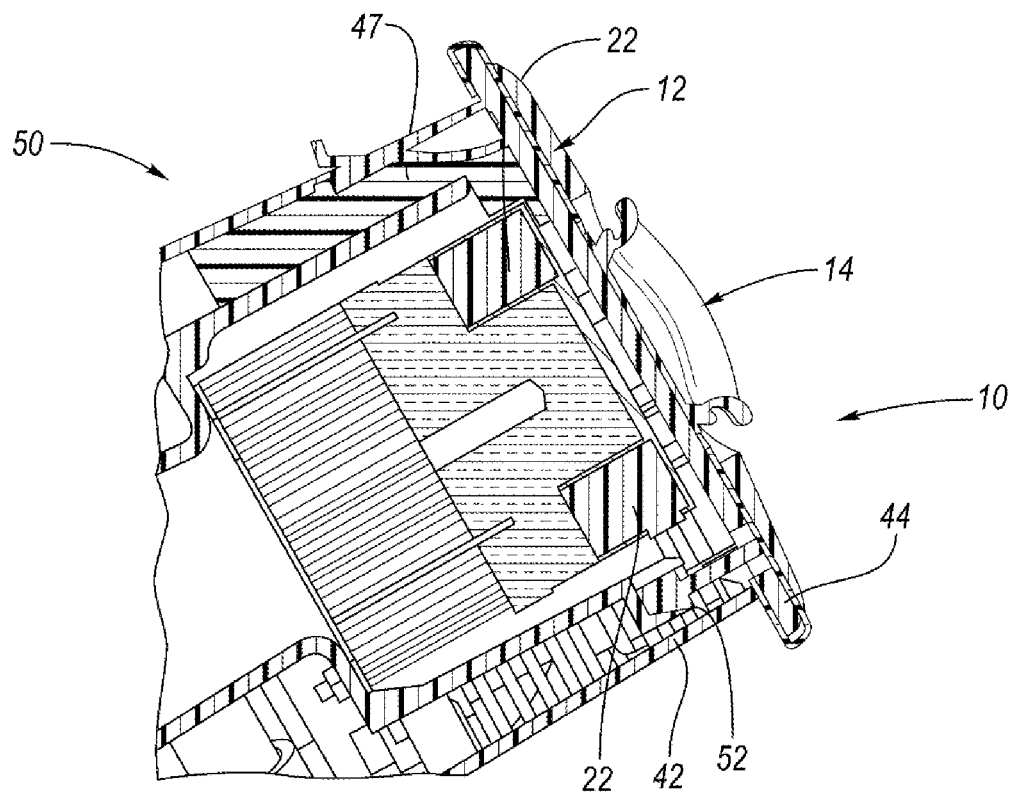
FIG. 13 is a cross-sectional view of the ocular positioning system with the positioning member engaging the housing, wherein detection by an optical sensor allows activation of the magnetic coil.

As best shown in FIG. 11, an inner side 46 of the cover 44 may include a spring arm 47 adjacent a first end 48 of the cover 44 and a detection arm 52 adjacent a second end 54 of the cover 44. The spring arm 47 may be received within the housing 32 to attach the first end 48 of the cover 44 to the housing 32. As shown in FIG. 12, in a rest position in the absence of force applied to the positioning member 10, the spring arm 47 acts to bias the positioning member 10 away from the proximal end 36 of the housing 32. In this figure, the detection arm 52 is not in proximity to the optical sensor 42, and thus the magnetic coil 22 is not capable of being activated.

The detection arm 52 is sized to be received adjacent the optical sensor 42 when the positioning member 10 (including the cover 44) is adjacent or engaged with the housing 32. When the optical sensor 42 detects the detection arm 52, the positioning member 10 is in proper and optimal position with respect to the magnetic coil 22 and the housing 32. When these conditions are met, the magnetic coil 22 is capable of being energized to allow treatment by the magnetic treatment apparatus 34. In one or more embodiments, a threshold detector 56 (FIG. 16) may be in electrical communication with the optical sensor 42 to compare the sensor output with a predetermined threshold value. If the sensor output exceeds the threshold value, the magnetic coil 22 is capable of receiving power so that the magnetic treatment apparatus 34 can be activated. Of course, other means of triggering the optical sensor 42 are also contemplated.

In one or more embodiments, the optical sensor 42 may continuously check for the presence of the detection arm 52 while the magnetic coil 22 is activated, such that if the optical sensor 42 no longer detects the detection arm 52 it will send a signal to cease power to the magnetic coil 22 and thus stop the treatment. Accordingly, the optical sensor 42 ensures that the positioning member 10, and therefore the subject's eye, is in the proper and optimal position for treatment before the magnetic coil 22 is capable of being activated, and the optical sensor 42 continues to ensure that the positioning member 10 and the subject's eye remains in proper and optimal position throughout the treatment.

As shown in FIGS. 10 and 11, the cover 44 may further include one or more locating tabs 58 at the first end 48 of the cover 44 and at the second end 54 of the cover 44. Corresponding channels 60 may be provided at the proximal end 36 of the housing 32 to receive the locating tabs 58 and guide the positioning member 10 into engagement with the housing 32 and to guide the detection arm 52 into proximity for detection by the optical sensor 42. The positioning member 10 may be moved into position with respect to the magnetic coil 22 and the housing 32 by the subject positioning his or her orbital region on the eyecup 14 and applying forward pressure to the eyecup 14 and positioning member 10 toward the housing proximal end 36.

Figure 14:
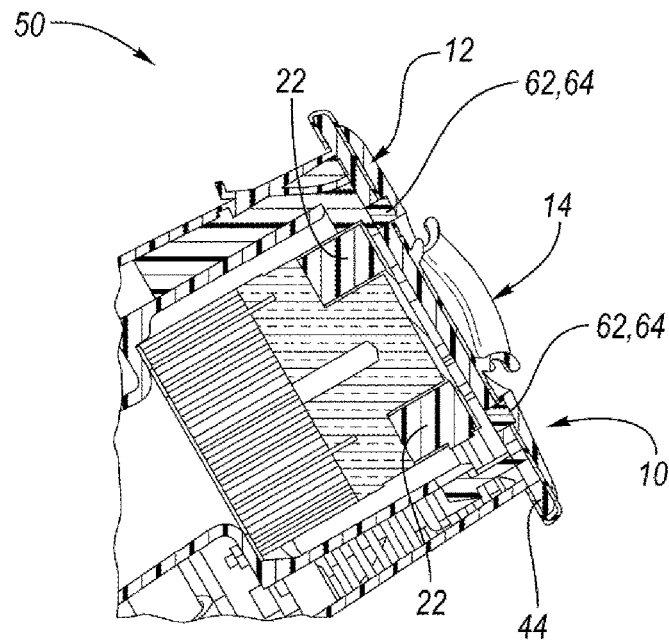
FIG. 14 is a cross-sectional view of the ocular positioning system with the positioning member engaging the housing, wherein detection by a pressure sensor or a proximity sensor allows activation of the magnetic coil.

Turning to FIG. 14, the at least one sensor may alternatively include one or more pressure sensors 62 disposed at the proximal end 36 of the housing 32. In the case of a pressure sensor, when the pressure sensor 62 detects force applied by contact from the positioning member 10 (including the cover 44), the positioning member 10 is in the proper and optimal position with respect to the magnetic coil 22 and the housing 32. The magnetic coil 22 is then capable of being activated to allow treatment by the magnetic treatment apparatus 34. As above, a threshold detector 56 may compare the sensor output with a predetermined threshold value. If the sensor output exceeds the threshold value, the magnetic coil 22 is capable of receiving power so that the magnetic treatment apparatus 34 can be activated. The pressure sensor 62 may continuously check for a force applied by the positioning member 10 while the magnetic coil 22 is activated, such that if the pressure sensor 62 no longer detects a sufficient force, it will send a signal to cease power to the magnetic coil 22 and thus stop the treatment. It is understood that the pressure sensor 62 could be triggered by a force applied by any portion of the positioning member 10 and is not limited to the embodiment described herein.

Alternatively, the one or more sensors in FIG. 14 could be proximity sensors 64. When the proximity sensor 64 detects the presence of the positioning member 10 (including the cover 44) in contact with or adjacent the housing 32, the positioning member 10 is in the proper and optimal position with respect to the magnetic coil 22 and the housing 32. The magnetic coil 22 is then capable of being activated to allow treatment by the magnetic treatment apparatus 34. The threshold detector 56 may compare the sensor output with a predetermined threshold value and, if the sensor output exceeds the threshold value, the magnetic coil 22 is capable of receiving power so that the magnetic treatment apparatus 34 can be activated. The proximity sensor 64 may continuously check for the presence of the positioning member 10 while the magnetic coil 22 is activated, such that if the proximity sensor 64 no longer detects the base 12, it will send a signal to cease power to the magnetic coil 22 and thus stop the treatment. The proximity sensor 64 may alternatively be configured to detect another portion of the positioning member 10 in order to trigger the sensor 64 and activate the magnetic coil 22 for treatment.

As described above, the positioning member 10 is designed such that the optimal position of the eye for effective treatment is when the eyecup 14 is in the position that activates the magnetic coil 22 via the sensor 42, 62, 64. Thus, if the subject positions their eye against the eyecup 14 but the positioning member 10 is not detected by the sensor 42, 62, 64 as being in the optimal position, the magnetic coil 22 will not be capable of being activated. The ocular positioning system 50 assures that the magnetic coil 22 will only be activated when the subject's eye is in optimal position, thus assuring effective treatment. In the present context, effective treatment may relate to obtaining the highest value of the electric field at a desired position of the eye or the orbital region.

Figure 15:
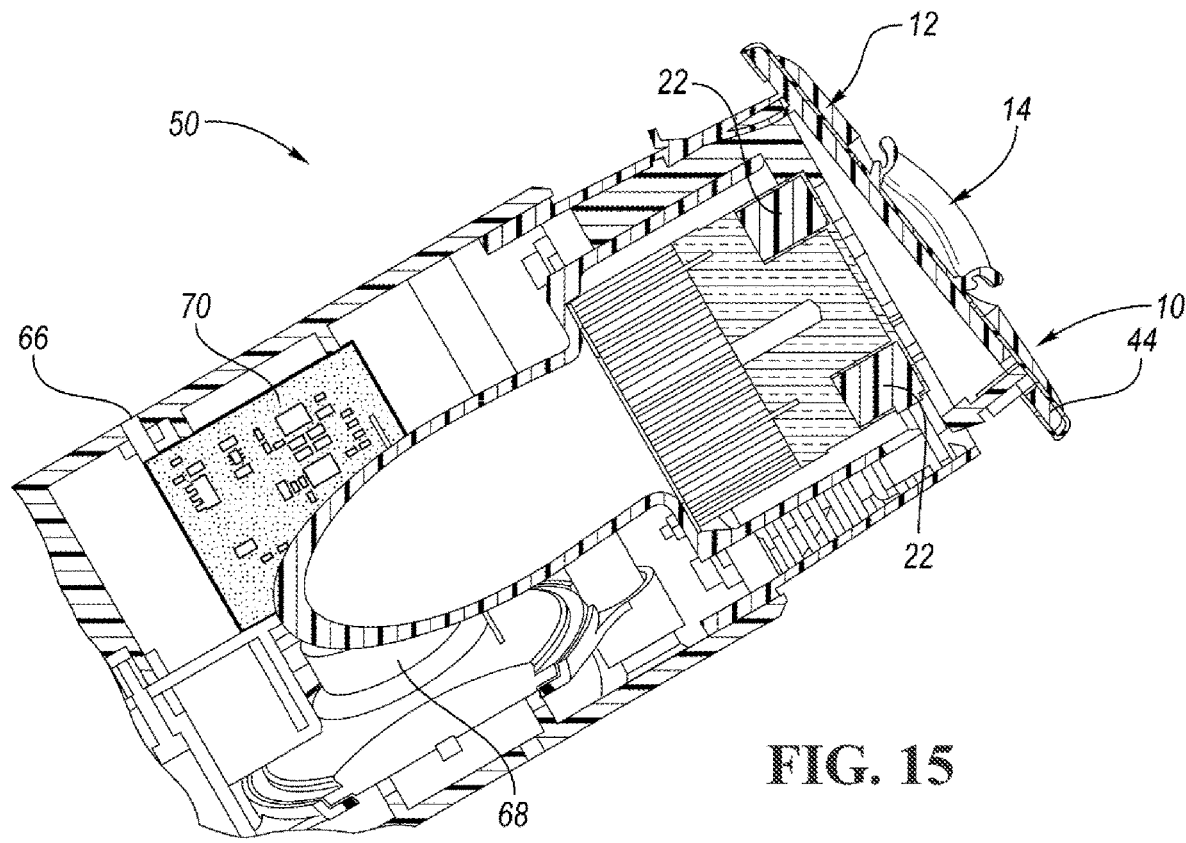
FIG. 15 is a cross-sectional view illustrating indicator features of the ocular positioning system.

FIG. 15 is a cross-sectional view illustrating possible indicator features of the ocular positioning system 50. In one or more embodiments, the ocular positioning system 50 can be equipped with an indicator which shows when the positioning member 10 is in proper position such that the magnetic coil 22 is capable of being activated. Such indicators may include a visual indicator such as, but not limited to, an LED 66. In addition to or as an alternative, an audio indicator, such as a speaker 68, may be employed. The indicators 66, 68 may be in electrical communication with a microcontroller unit 70 which controls their activation.

Figure 16:
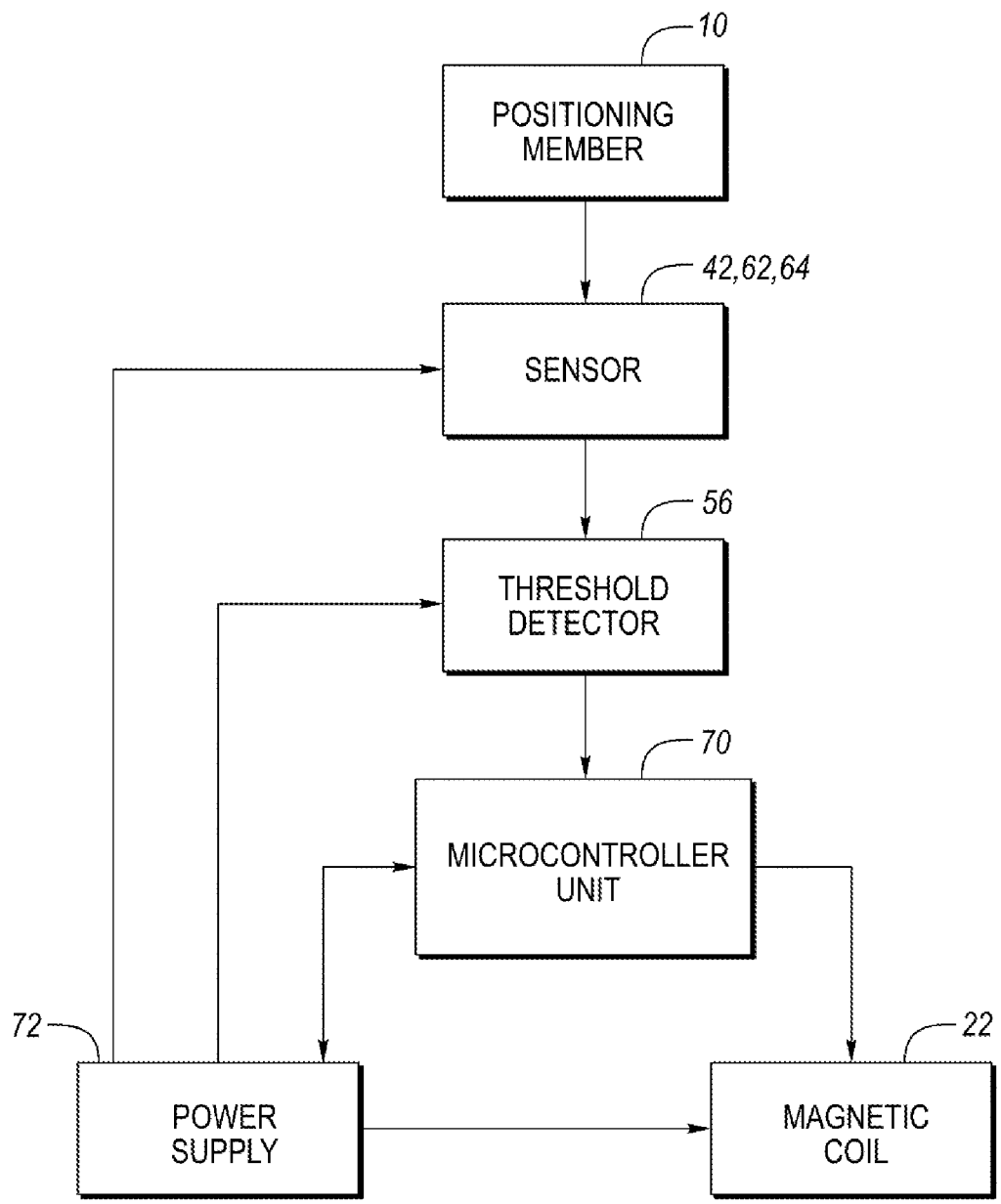
FIG. 16 is a block diagram depicting various mechanical and electrical components of the ocular positioning system.

FIG. 16 is a block diagram depicting the mechanical and electrical components of the ocular positioning system 50. As described in connection with the various embodiments disclosed above, the sensor 42, 62, 64 (e.g. optical, pressure, proximity, etc.) detects the positioning member 10. The sensor 42, 62, 64 is in electrical communication with a threshold detector 56 which compares the sensor signal to a predetermined threshold value. The threshold detector 56 is in electrical communication with the microcontroller unit 70 which selectively controls activation of the magnetic coil 22 based upon whether the predetermined threshold value is met. The microcontroller unit 70 can control a power supply 72 to provide or cease power to the magnetic coil 22, and may also control treatment parameters of the magnetic coil 22 directly.

The ocular positioning system 50 disclosed herein may be used in a method for improving the effectiveness of the eye treatment by a magnetic treatment apparatus 34, wherein the method may include the steps of determining the optimal treatment positioning of a subject's eye and surrounding tissue in relation to the magnetic coil 22 of the magnetic treatment apparatus 34 to target the same area for each treatment; fitting the subject with an eyecup 14 which conforms to the subject's anatomy in a manner which enables positioning the subject's eye in an optimal treatment position; and activating the magnetic coil 22 by positioning the subject's eye in the optimal treatment position.

The ocular positioning system 50 disclosed herein may also be used in a method for the treatment of an eye disorder by a magnetic treatment apparatus 34, wherein the method may include the steps of determining the magnetic treatment protocol; programming the protocol into a magnetic treatment apparatus 34; determining the optimal treatment positioning of a subject's eye in relation to the magnetic coil 22 of the magnetic treatment apparatus; fitting the subject with an eyecup 14 which conforms to their anatomy in a manner which enables positioning their eye in optimal treatment position; and activating the magnetic coil 22 by positioning the subject's eye in the optimal treatment position.

The ocular positioning system disclosed herein maintains the optimal positioning of a subject's eye during noninvasive, non-contact magnetic treatment while maintaining the subject's comfort throughout the treatment. Accurately positioning the eye in such treatments improves the effectiveness of the treatment, and in the ocular positioning system the activation of the magnetic field is dependent on the accurate and optimal positioning of the subject's eye. Thus, treatment will only be administered when the subject's eye is the optimal position and the activation of the magnetic field is initiated by the subject and does not require additional intervention by a medical professional.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An ocular positioning system for use with a magnetic treatment apparatus for treating an eye of a subject, the magnetic treatment apparatus including a magnetic coil for generating a magnetic field and an electrical field, the ocular positioning system comprising:
   a housing having a proximal end and a distal end, wherein the magnetic coil is disposed in the housing near the proximal end; and
   a positioning member at least partially attached to the housing proximal end, the positioning member including a base and an eyecup coupled thereon, the eyecup configured to receive an orbital region of the subject.

2. The ocular positioning system of claim 1, wherein the positioning member further includes a cover arranged to be received on the housing proximal end, wherein the base is removably attached to the cover.

3. The ocular positioning system of claim 1, wherein the positioning member includes a spring arm extending therefrom, wherein the spring arm is arranged to be received within the housing to bias the positioning member away from the proximal end of the housing.

4. The ocular positioning system of claim 1, further comprising an optical sensor in electrical communication with the magnetic coil.

5. The ocular positioning system of claim 4, wherein the positioning member includes a detection arm extending therefrom, wherein the detection arm is arranged to be detected by the optical sensor when the positioning member is adjacent the proximal end of the housing.

6. The ocular positioning system of claim 1, further comprising a pressure sensor in electrical communication with the magnetic coil, the pressure sensor being disposed at the proximal end of the housing to detect when the positioning member is adjacent the proximal end of the housing.

7. The ocular positioning system of claim 1, further comprising a proximity sensor in electrical communication with the magnetic coil, the proximity sensor being disposed at the proximal end of the housing to detect when the positioning member is adjacent the proximal end of the housing.

8. The ocular positioning system of claim 1, further comprising at least one indicator in electrical communication with at least one sensor to indicate when the positioning member is in position for activation of the magnetic coil.

9. The ocular positioning system of claim 1, further comprising at least one sensor monitoring for detection of the positioning member while the magnetic coil is activated.

10. The ocular positioning system of claim 1, further comprising a threshold detector in electrical communication with at least one sensor, wherein if the threshold detector determines that an output of the at least one sensor exceeds a predetermined threshold value then the magnetic coil is capable of being activated.

11. The ocular positioning system of claim 1, wherein the eyecup includes a wall extending upwardly from the base and configured to receive an orbital region of the subject.

12. The ocular positioning system of claim 1, wherein a distance between a center of the eyecup and a center of the base is approximately 3 mm.

13. The ocular positioning system of claim 11, wherein the wall includes a vent.

14. The ocular positioning system of claim 11, wherein the wall includes a medial wall portion and a lateral wall portion which differ in height.

15. The ocular positioning system of claim 1, wherein the positioning member is specifically designed for use with one of a left eye or a right eye of the subject.

16. A magnetic treatment apparatus for treating an eye of a subject, comprising:
   a housing having a proximal end and a distal end;
   a magnetic coil disposed in the housing near the proximal end;
   a positioning member at least partially attached to the housing proximal end, the positioning member including a base and an eyecup coupled thereon, the eyecup configured to receive an orbital region of the subject.

17. The magnetic treatment apparatus of claim 16, wherein the positioning member includes a spring arm extending therefrom, wherein the spring arm is arranged to be received within the housing to bias the positioning member away from the proximal end of the housing.

18. The magnetic treatment apparatus of claim 16, further comprising at least one indicator in electrical communication with at least one sensor to indicate when the positioning member is in position for activation of the magnetic coil.

19. The magnetic treatment apparatus of claim 16, further comprising a threshold detector in electrical communication with at least one sensor, wherein if the threshold detector determines that an output of the at least one sensor exceeds a predetermined threshold value then the magnetic coil is capable of being activated.

* * * * *